United States Patent
Wynn et al.

(10) Patent No.: US 10,220,105 B2
(45) Date of Patent: Mar. 5, 2019

(54) RADIOLABELLING METHOD

(71) Applicant: GE Healthcare Limited, Buckinghamshire (GB)

(72) Inventors: Duncan George Wynn, Amersham (GB); Steven Michael Fairway, Oslo (NO); Matthias Eberhard Glaser, Amersham (GB); Ian Newington, High Wycombe (GB); Gareth Edwin Smith, Amersham (GB); Imtiaz Ahmed Khan, Amersham (GB); Julian Grigg, Amersham (GB)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 15/318,122

(22) PCT Filed: Dec. 16, 2014

(86) PCT No.: PCT/EP2014/078043
§ 371 (c)(1),
(2) Date: Dec. 12, 2016

(87) PCT Pub. No.: WO2016/000798
PCT Pub. Date: Jan. 7, 2016

(65) Prior Publication Data
US 2017/0106104 A1 Apr. 20, 2017

(30) Foreign Application Priority Data
Jun. 30, 2014 (GB) .................................. 1411571.1

(51) Int. Cl.
| | |
|---|---|
| *C07D 215/20* | (2006.01) |
| *A61K 51/04* | (2006.01) |
| *C07D 401/04* | (2006.01) |
| *B01D 15/32* | (2006.01) |
| *B01J 19/24* | (2006.01) |

(52) U.S. Cl.
CPC ........ *A61K 51/0455* (2013.01); *B01D 15/325* (2013.01); *B01J 19/24* (2013.01); *C07D 215/20* (2013.01); *C07D 401/04* (2013.01); *B01J 2219/24* (2013.01)

(58) Field of Classification Search
CPC .. C07D 215/20; C07D 401/04; B01D 15/325; B01J 19/24; B01J 2219/24; A61K 51/0455
See application file for complete search history.

(56) References Cited

U.S. PATENT DOCUMENTS

| | | | |
|---|---|---|---|
| 9,061,996 B2 | 6/2015 | Mantzilas et al. | |
| 9,249,101 B2* | 2/2016 | Kudo | A61K 9/0019 |
| 9,452,985 B2* | 9/2016 | Kudo | A61K 9/0019 |
| 9,701,637 B2* | 7/2017 | Kudo | A61K 9/0019 |

FOREIGN PATENT DOCUMENTS

| | | |
|---|---|---|
| CN | 103380118 A | 10/2013 |
| EP | 2634177 A1 | 9/2013 |
| JP | 2014506874 A | 3/2014 |
| JP | 5928901 B2 | 6/2016 |
| JP | 6145107 B2 | 6/2017 |
| RU | 2476423 C2 | 1/2012 |
| WO | 2012057312 A1 | 5/2012 |
| WO | 2013/079578 A1 | 6/2013 |
| WO | 2013079578 A1 | 6/2013 |

OTHER PUBLICATIONS

Fortt, Nuclear Medicine and Biology, vol. 39, 1000-1005, 2012.*
Okamura et al., "Novel 18F-Labeled Arylquinoline Derivatives for Noninvasive Imaging of Tau Pathology in Alzheimer Disease", The Journal of Nuclear Medicine, vol. 54, No. 8, Aug. 1, 2013, pp. 1420-1427.
Graham et al., "Enantioselective Radiosynthesis of Positron Emission Tomography (PET) Tracers Containing [18F] Fluorohydrins", Journal of the American Chemical Society, vol. 136, No. 14, Apr. 9, 2014, pp. 5291-5294.
International Search Report and Written Opinion regarding International Application No. PCT/EP2014/078043, dated Apr. 8, 2015, 11 pages.
Search Report issued in corresponding Russian Application No. 2016148821/04(07844) dated Jul. 20, 2018.
Office Action issued in corresponding Russian Application No. 2016148821/04(078440) dated Jul. 23, 2018.
Okamura, et al., "Novel 18F-Labeled Arylquinoline Derivatives for Noninvasive", 2013, vol. 54, No. 8, p. 1420-1427.
Thomas, et al., "Enantioselective Radiosynthesis of Positron Emission Topography (PET) Tracers Containing [18F] Fluorohydrins", 2014, vol. 136, No. 14, p. 5291-5294.
China Office Action in correspondence to CN Application No. 201480080272.5, dated Aug. 28, 2018.
China First Search Report in correspondence to CN Application No. 201480080272.5, dated Jul. 31, 2018.
Japanese Office Action corresponding to JP Application No. 2016-575188, dated Aug. 7, 2018.
Fortt, et al., "Automated GMP Synthesis of [18F] ICMT-11 for In Vivo Imaging of Caspase-3 Activity", Nuclear Medicine and Biology, 2012, pp. 1000-1005.

* cited by examiner

*Primary Examiner* — D Margaret M Seaman
(74) *Attorney, Agent, or Firm* — Arent Fox LLP

(57) ABSTRACT

The present invention relates to the field of radiopharmaceuticals for in vivo imaging, in particular to automated methods for the preparation and purification of $^{18}$F-labelled tau imaging radiotracers. Also provided are interchangeable cassettes useful in the methods, and the use of automated synthesizers and cassettes in the methods.

16 Claims, 2 Drawing Sheets

RADIOLABELLING METHOD

CROSS-REFERENCE TO RELATED APPLICATIONS

This application is a filing under 35 U.S.C. 371 of international application number PCT/EP2014/078043, filed Dec. 16, 2014, which claims priority to GB application number 1411571.1, filed Jun. 30, 2014, the entire disclosures of each of which are hereby incorporated by reference.

FIELD OF THE INVENTION

The present invention relates to the field of radiopharmaceuticals for in vivo imaging, in particular to automated methods for the preparation and purification of $^{18}F$-labelled tau imaging radiotracers. Also provided are interchangeable cassettes useful in the methods, and the use of automated synthesizers and cassettes in the methods.

BACKGROUND TO THE INVENTION

Tau is a phosphoprotein having a physiological function of binding to tubulin to stabilise microtubules. The degree of tau phosphorylation determines the binding affinity to microtubules-tau hyperphosphorylation leads to weaker microtubule binding. There is growing evidence that tau malfunction is implicated in, or triggers neurodegeneration and dementia. There is therefore significant interest in the molecular imaging of tau in vivo.

EP 1574500 A1 (BF Research Institute Inc.) discloses diagnostic probes for Tau proteins which comprise optionally radiolabelled compounds of structure:

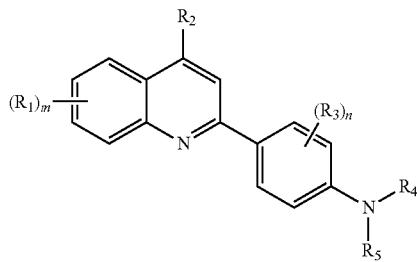

wherein:
$R_1$, $R_2$, and $R_3$ independently are H, Hal, OH, COOH, $SO_3H$, $NH_2$, $NO_2$, CO—NH—$NH_2$, $C_{1-4}$ alkyl or O—$C_{1-4}$ alkyl, wherein two $R_1$ groups together, may form a benzene ring;

$R_4$ and $R_5$ are independently H or $C_{1-4}$ alkyl; and m and n are independently integers of value 0 to 4.

WO 2012/067863 discloses that quinolines can be radiolabelled with radioisotopes suitable for PET or SPECT imaging to provide Tau imaging agents. WO 2012/067863 mentions that automated methods optionally including cassettes can be used, but does not describe particular precursors, methods or cassettes.

WO 2012/057312 A1 discloses Tau imaging radiotracers which are radiolabelled compounds of Formula (I):

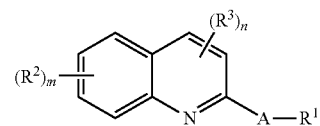

wherein
A is

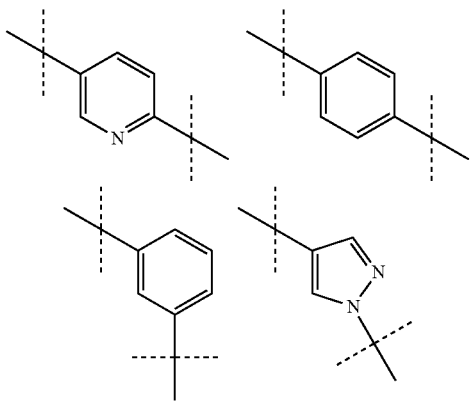

$R^1$ is Hal, a —C(=O)-lower alkyl group (said alkyl group may be each independently substituted with one or more substituents selected from the group consisting of $NR^aR^b$, Hal, and OH), a lower alkyl group (said alkyl group may be each independently substituted with one or more substituents selected from the group consisting of Hal and OH), an —O-lower alkyl group (said alkyl group may be each independently substituted with one or more substituents selected from the group consisting of Hal and OH), or wherein
$R^4$ and $R^5$ are each independently H, a lower alkyl group, or a cycloalkyl group, or $R^4$, $R^5$, and the nitrogen atom to which they are attached are together form a 3- to 8-membered nitrogen-containing aliphatic ring (one or more carbon atoms constituting said nitrogen-containing aliphatic ring may be replaced by a N, S or O atom, and when the carbon atom is replaced by a N atom, said N atom may be substituted with a lower alkyl group), or $R^4$ and the nitrogen atom to which it is attached, together with the ring A, form an 8- to 16-membered nitrogen-containing fused bicyclic ring system (one or more carbon atoms constituting said nitrogen-containing fused bicyclic ring system may be replaced by a N, S or O atom, and when the carbon atom is replaced by a nitrogen atom, said nitrogen atom may be substituted with a lower alkyl group), and $R^5$ is H, a lower alkyl group, or a cycloalkyl group, where a solid line intersected with a broken line designates a linkage with another structural portion in the general formulae above, $R^2$ or $R^3$ is each independently Hal, OH, COOH, $SO_3H$, $NO_2$, SH, $NR^aR^b$, a lower alkyl group (said alkyl group may be each independently substituted with one or more substituents selected from the group consisting of Hal and OH), or an —O-lower alkyl group (said alkyl group may be each independently substituted with one or more substituents selected from the group consisting of Hal and OH), the ring A is unsubstituted or substituted with $R^6$ (wherein $R^6$ is one or more substituents independently selected from the group consisting of Hal, OH, COOH, $SO_3H$, $NO_2$, SH, $NR^aR^b$, a lower alkyl group (said alkyl group may be each independently substituted with one or more substituents selected from the group consisting of Hal and OH), and an —O-lower alkyl group (said alkyl group may be each independently substituted with one or more substituents selected from the group consisting of Hal, OH, and an —O-lower alkyl group-O-lower alkyl group (said alkyl group may be each independently substituted with Hal))), $R^a$ and $R^b$ are independently H or a lower alkyl group (said alkyl group may be each independently substituted with one or more substituents selected from the group consisting of Hal and OH), m is an integer from 0 to 4, and n is an integer from 0 to 4.

WO 2012/057312 A1 teaches that the $^{18}$F-radiotracers are purified using a combination of Sep-Pak cartridges followed by semi-preparative HPLC.

Okamura et al [J. Nucl. Med., 54(8), 1420-1427 (2013)] disclose that $^{18}$F-arylquinolines, in particular $^{18}$F-THK-5105 and $^{18}$F-THK-5117 are novel imaging agents for imaging tau pathology in Alzheimer's disease. Okamura et al use the following precursors and radiofluorination method:

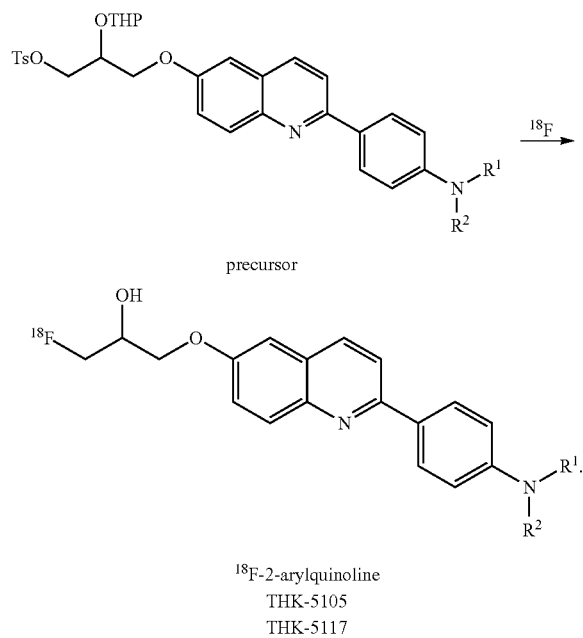

precursor $^{18}$F-2-arylquinoline
THK-5105
THK-5117

$R^1 = R^2 = CH_3$ $R^1 = H, R^2 = CH_3$

Okamura et al use a manual radiolabelling reaction, plus semi-preparative HPLC for purification of the radiotracer.

Blom et al [J. Radioanal. Nucl. Chem., 299, 265-270 (2014)] teach that the radiotracer

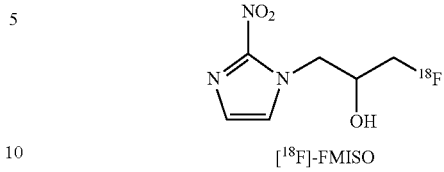

[$^{18}$F]-FMISO

[$^{18}$F]-FMISO, which also incorporates a fluorohydroxypropyl group, can be prepared via an automated radiosynthesis. Blom et al studied various solid-phase extraction (SPE) columns together with the chemical and radiochemical impurities, and concluded that a hydrophilic-lipophilic balanced (HLB), polymer-based cartridge was superior to both a mixed mode (MCX) cartridge and a Sep-Pak C18 cartridge.

There is therefore still a need for alternative and/or improved methods of preparing and purifying the tau imaging agents of WO 2012/057312 A1 and Okamura et al.

The Present Invention

The precursor synthesis method of the present invention provides an automated synthesis of quinoline-based [$^{18}$F]-labelled tau radiotracers. The automated method includes an automated purification methodology, which uses only solid-phase extraction (SPE) avoids the need for HPLC as taught by the prior art. The purification method is thus fast (ensuring minimal loss of tracer due to radioactive decay), and reproducible. The purification method has also been adapted to work effectively across the wide range of operating temperatures (ca. 15-37° C.) that may be found in practice in hot cells where radiosynthesizer apparatus is located.

The method comprises the use of an interchangeable, single-use cassette which is adapted to make the radiosynthesis even more convenient for the operator, since minimal operator intervention is required. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, as well as being tamper and abuse resistance.

DETAILED DESCRIPTION OF THE INVENTION

In a first aspect, the present invention provides an automated method of preparation of an $^{18}$F-labelled radiotracer of Formula (II), which comprises:

(i) provision of an automated synthesizer apparatus which comprises a microprocessor, and an interchangeable, disposable cassette which comprises a reaction vessel, a supply of solvents suitable for the preparation and purification of said radiotracer, and a supply of the precursor of Formula (I):

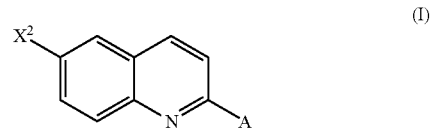

(ii) microprocessor-controlled transfer of said precursor of Formula (I) from step (i) to said reaction vessel, followed by reaction of said precursor with [$^{18}$F]-fluoride in a suitable solvent, and removal of the $Pg^1$ protecting group, to give the $^{18}$F-labelled radiotracer of Formula (II):

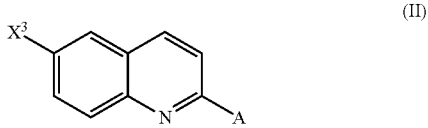

(II)

wherein:
A is chosen from:

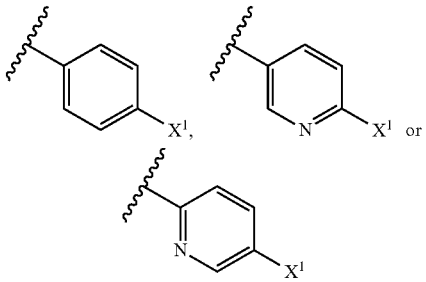

$X^1$ and $X^2$ are independently an $X^a$ or an $X^b$ group;
$X^3$ is an $X^a$ or an $X^c$ group;
$X^a$ is —$NR^1R^2$;
$X^b$ is

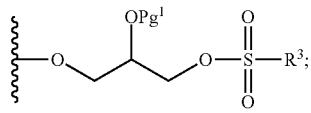

$X^c$ is

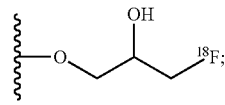

$R^1$ and $R^2$ independently comprise H or $C_{1-4}$ alkyl, or $R^1$ and $R^2$ together with the N atom and optionally the phenyl ring to which they are attached comprise a 5- or 6-membered nitrogen-containing aliphatic or heteroaromatic ring, optionally incorporating one further heteroatom chosen from —O—, —S—, =N— and —$NR^a$—, where $R^a$ is H or $C_{1-4}$ alkyl;
$R^3$ is $C_{1-4}$ alkyl, $C_{1-4}$ haloalkyl, $C_{5-8}$ aryl or $C_{6-12}$ aralkyl;
$Pg^1$ is an alcohol protecting group;
provided that in Formula (I), one $X^b$ group is present, and in Formula (II), one $X^c$ group is present.

Thus, in the method of the first aspect, the $X^b$ group of the precursor of Formula (I) contains a reactive site (sulfonate ester group), which undergoes nucleophilic radiofluorination with [$^{18}$F]-fluoride ion in step (ii) to give the corresponding $X^c$ substituent of the radiotracer product of Formula (II). The microprocessor control of step (ii) is achieved via the microprocessor of said automated synthesizer apparatus. The provisos of one $X^b$ or $X^c$ group being present imply that:
in Formula (I), one of $X^1$ and $X^2$ is an $X^a$ group and the other is an $X^b$ group;
in Formula (II), one of $X^1$ and $X^3$ is an $X^a$ group and the other is an $X^c$ group;

The term "radiotracer" has its' conventional meaning and refers to a radiopharmaceutical used to trace a physiological or biological process without affecting it. The term "radiopharmaceutical" has its' conventional meaning and refers to a radiolabelled compound administered to the mammalian body in vivo for the purpose of imaging or therapy.

By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette. The automated synthesizer comprises a microprocessor, which controls the operation of the synthesizer apparatus, including the operation of any associated cassette.

By the term "cassette" is meant a unit piece of apparatus designed such that the whole unit fits removably and interchangeably onto an automated synthesizer apparatus (as defined above), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. solid phase extraction or SPE). The cassette always comprises a reaction vessel. Such reaction vessels are preferably 1 to 10 cm$^3$, most preferably 2 to 5 cm$^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Preferred automated synthesizers of the present invention comprise a disposable or single-use cassette which comprises all the reagents, reaction vessels and apparatus necessary to carry out the preparation of a given batch of radiofluorinated radiopharmaceutical. The cassette means that the automated synthesizer has the flexibility to be capable of making a variety of different radiopharmaceuticals with minimal risk of cross-contamination, by simply changing the cassette. The cassette approach also has the advantages of simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, as well as being tamper and abuse resistance.

By the term "precursor" refers to a 'radiolabelling precursor' which means a non-radioactive compound suitable for reaction with a supply of a radioisotope in a suitable solvent, to give the radiolabeled compound of interest in the minimum numbers of steps. Thus, the precursor is designed such that the chemical and radioactive yield is optimised, and the number of steps involving the handling of radioactivity is minimized. The precursor is particularly suitable for radiolabelling with $^{18}$F.

By the term "protecting group" is meant a removable group which inhibits or suppresses undesirable chemical reactions, and which is designed such that it can be both attached and removed to/from the functional group in question under mild enough conditions that do not modify or compromise the rest of the molecule. After deprotection the desired product is obtained. The use of protecting groups is described in *Protective Groups in Organic Synthesis*, 4th Edition, Theorodora W. Greene and Peter G. M. Wuts, [Wiley Blackwell, (2006)]. The term "deprotection" has its conventional meaning in the field of chemistry and/or radiochemistry, i.e. the removal of a protecting group.

The alcohol protecting group ($Pg^1$) of the first aspect protects the secondary alcohol group of the $X^b$ group. Suitable $Pg^1$ groups include ethers (alkyl, aryl, aralkyl, or silyl); esters or carbonates. Further details of alcohol protecting groups are provided by Greene and Wuts (cited above).

When $R^1$ and $R^2$ together with the N atom and optionally the phenyl ring to which they are attached comprise a 5- or 6-membered nitrogen-containing aliphatic or heteroaromatic ring, that means that the 5- or 6-membered ring incorporating one or more of N, $R^1$ and $R^2$ may either be a substituent on the phenyl ring, or be fused with the phenyl ring bearing —$NR^1R^2$. Examples of the former would be piperidine or morpholine rings singly bonded to the phenyl ring. A preferred example of a fused ring is when $X^a$ is:

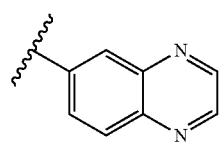 [SMILES: *c1ccc2nccnc2c1]

The $X^b$ group incorporates a sulfonate ester group —$OSO_2R^3$. Such sulfonate esters are important leaving groups in nucleophilic substitution, and the reactivity of the sulfonate ester towards nucleophilic substitution can be adjusted depending on the choice of $R^3$ [M. B. Smith and J. March, *March's Advanced Organic Chemistry*, Fifth Edition, John Wiley & Sons Inc., (2001), pages 445-449].

The "suitable solvent" for step (ii), includes: acetonitrile, a $C_{1-4}$ alkyl alcohol, dimethylformamide, tetrahydrofuran, or dimethylsulfoxide, or aqueous mixtures of any thereof.

Preferred Aspects

In the method of the first aspect, step (ii) is preferably carried out by:
(a) reaction of the precursor of Formula (I) with [$^{18}$F]-fluoride in a suitable solvent, to give an $^{18}$F-labelled intermediate of Formula (III):

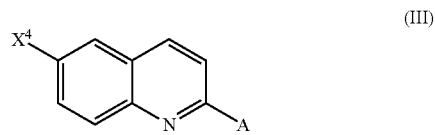

wherein
$A^1$ is chosen from:

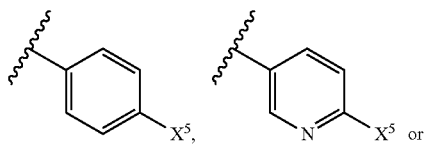

$X^4$ and $X^5$ are each independently an $X^a$ or $X^d$ group; where $X^d$ is:

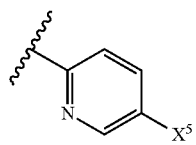

provided that, in Formula (III) one $X^d$ group is present; then:—
(b) removal of the $Pg^1$ protecting group from said intermediate to give the $^{18}$F-labelled radiotracer of Formula (II).

In the method of the first aspect, $X^2$ is preferably $X^b$, such that the precursor is of Formula (IA):

(IA)

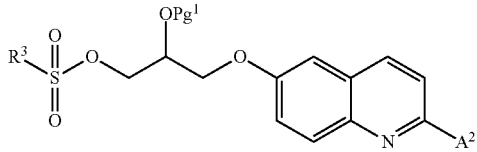

and the radiotracer product is of Formula IIA:

(IIA)

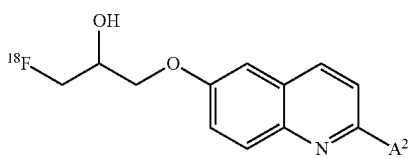

where $A^2$ is chosen from:

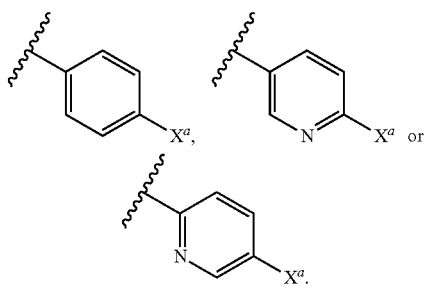

In the method of the first aspect, the precursor is more preferably the S-enantiomeric form of Formula (IB):

(IB)

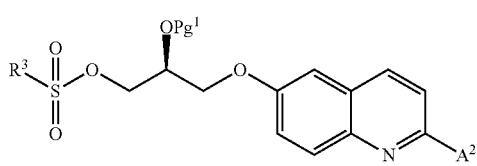

and the radiotracer product is the S-enantiomer of Formula (IIB):

(IIB)

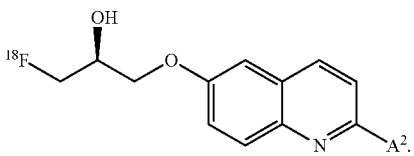

The precursor may be enriched in said S-enantiomeric form, to exceed the 50:50 content of the racemic mixture, and is preferably in substantially pure form. In the method of the first aspect, A in Formulae (I), (IA), (IB), (II), (IIA), (IIB) and (III) is preferably an $A^2$ group of formula:

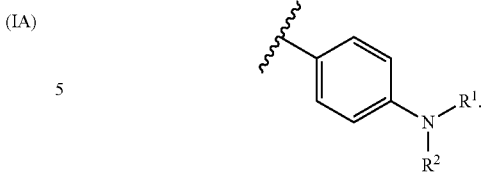

wherein —$NR^1R^2$ is more preferably —$NHCH_3$ or —$N(CH_3)_2$, and most preferably —$NHCH_3$.

In the method of the first aspect, $Pg^1$ is preferably a $Pg^{1a}$ group, wherein $Pg^{1a}$ comprises:
(i) —$R^c$;
(ii) —$Ar^1$;
(iii) —$CH(Ar^1)_2$;
(iv) —$C(Ar^1)_3$;
(v) tetrahydropyranyl optionally substituted with one or more substituents chosen from Hal and $OCH_3$;
(vi) —$CH_2OR^b$;
(vii) —$SiR^d_3$;
(viii) —(C=O)$R^d$;
(ix) —(C=O)$OR^e$ wherein $R^e$ is H, $R^d$, $C_{1-4}$ haloalkyl or vinyl; or
(x) —(C=O)$NHR^d$;
wherein:
each $R^b$ is independently $R^d$ or $C_{2-4}$ alkoxyalkyl optionally substituted with one or more Hal;
each $R^c$ is independently $C_{1-4}$ alkyl;
each $R^d$ is independently $R^c$ or $Ar^1$; and
$Ar^1$ is independently benzyl or phenyl optionally substituted with one or more substituents chosen from Hal, $CH_3$, $OCH_3$, $NO_2$ or —$N(CH_3)_2$.

$Pg^1$ is most preferably tetrahydropyranyl.

In the method of the first aspect, $R^3$ is preferably chosen from: —$CH_3$, —$CF_3$, —$C_4F_9$, —$CH_2CF_3$, —$C_6H_4$—$CH_3$, —$C_6H_4$—$NO_2$ or —$C_6H_4$—Br. $R^3$ is more preferably —$C_6H_4$—$CH_3$.

In the method of the first aspect, the cassette preferably further comprises one to three C18-reverse phase solid phase extraction (SPE) columns, and said method further comprises step (iii):

(iii) microprocessor-controlled SPE purification of the $^{18}$F-labelled radiotracer of Formula (II) from step (ii) using said cassette SPE columns, and the solvent(s) of said cassette.

The use of SPE avoids the need for HPLC purification, which is typically carried out manually, and thus means that the radiosynthesis and purification of the radiotracer can be carried out in a fully-automated manner using an appropriate cassette. Thus, the purification method of the present invention preferably does not comprise HPLC. In the SPE purification of the first aspect, the C18-reverse phase SPE column is preferably silica-based, and is thus preferably a C18-silica SPE column and is more preferably a tC18+ silica SPE column Polymer-based SPE cartridges are less preferred, since HLB type cartridges have been found to bind the radiotracers of the present invention so strongly that elution becomes difficult. Reverse phase SPE cartridges suitable for use in the present invention can be obtained from Waters Limited (730-740 Centennial Court, Centennial Park, Elstree, Hertfordshire, UK). A suitable size of SPE column for use in the present invention is 900 mg.

It is well-established that chromatography such as the SPE purification process is subject to variations depending on the ambient temperature. So-called "hot cells" are used for the production of PET radiotracers. These are enclosures with the necessary facilities to carry out the radiosynthesis, but also having radiation-shielding and suitable ventilation to protect the operator. Such hot cells range from large units that are able to maintain room temperature (18° C.-22° C.) despite the large amount of electrical equipment contained within them, to very small units that can reach operating temperatures of 30° C.-40° C. The present inventors have found that (see Example 2), elevated temperatures affect the SPE purification such that the radiotracer product elutes more quickly. As a result, satisfactory purification of the radiotracer of Formula (II) can be achieved at temperatures ranges of 15-25° C. using two 900 mg size SPE columns. At higher temperatures, however, of 15 to 40° C. three SPE columns are necessary. Hence, the cassette and SPE method of the first aspect preferably comprises the use of three 900 mg size SPE columns, since that permits effective purification across the range of operating temperatures (ca. 15 to 40° C.) likely to be found in radiosynthesis hot cells. Whilst it is possible that a smaller number of larger SPE columns could be used, such larger columns are less likely to be of a size compatible with automated synthesizer apparatus.

In the SPE purification of the first aspect, the C18-reverse phase SPE column is eluted with an elution volume in the range 9-12 mL, preferably 10.5 to 11.5 mL. In the SPE purification method of the first aspect, the SPE columns are first eluted with an aqueous, water-miscible organic solvent to remove impurities, and then eluted with ethanol to elute the radiotracer of Formula (II). The "aqueous, water-miscible organic solvent" refers to a mixture of water and the water-miscible organic solvent. Suitable such organic solvents include acetonitrile, ethanol, THF, isopropanol and methanol, and are preferably chosen from: acetonitrile, ethanol and THF, more preferably acetonitrile and ethanol, most preferably acetonitrile. The aqueous acetonitrile solvent, i.e. the acetonitrile/water solvent mixture is suitably in the range 20 to 50% v/v, and is preferably in the range 25 to 45%, more preferably in the range 35 to 40%. 40% aqueous acetonitrile is most preferred.

By way of illustration of the SPE purification, the following discussion refers to Compound 1 and Precursor 1 (see Scheme 1)—but the same principles apply for other compounds within the scope of the first aspect.

Scheme 1

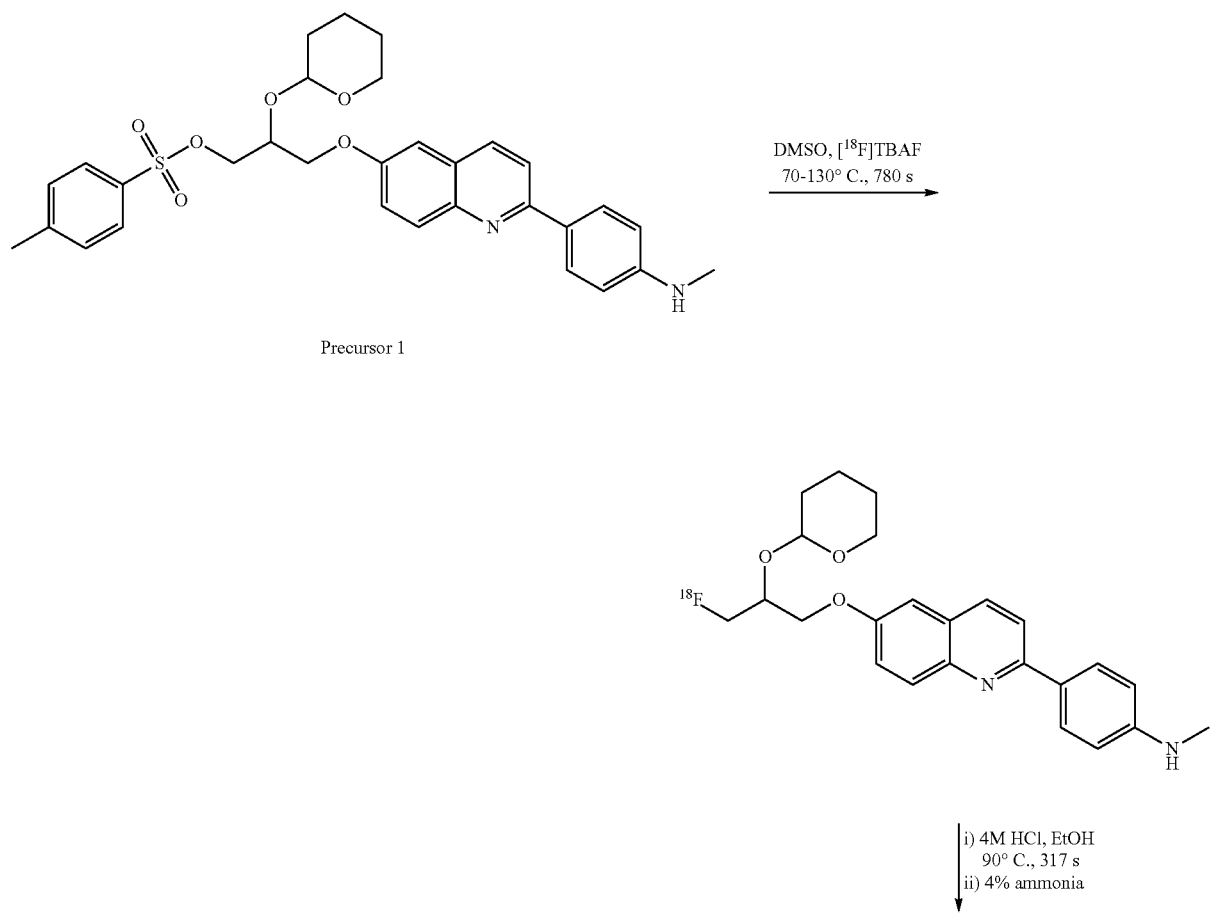

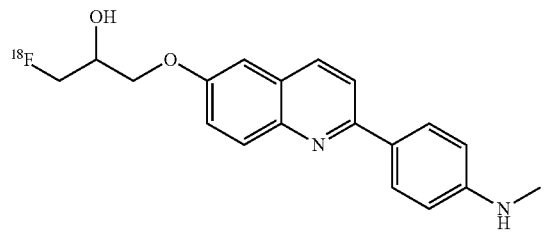

Compound 1

Under the reaction conditions, there is a significant chemical excess of Precursor 1 over the chemical amount of [$^{18}$F]-fluoride present. Under the reaction conditions, Precursor 1 also reacts and at least a portion thereof is converted primarily to the diol (Impurity A; see structures below), and possibly some of Impurity B. The largest impurity is Impurity A, which elutes and is removed when the SPE columns are eluted with aqueous acetonitrile.

Precursor 1 is significantly more lipophilic than Compound 1, and remains bound to SPE columns—when eluted with either aqueous acetonitrile or ethanol. Compound 1 does not elute when the SPE columns are washed with 10-12 mL of aqueous acetonitrile, but is subsequently eluted when pure ethanol is used to elute the SPE column(s). In this manner, Compound 1 is purified. Impurity B is observed less frequently, but any present remains bound to the SPE column under the conditions of the invention.

The method of the first aspect preferably further comprises, in addition to purification step (iii), the following steps:
(iv) optionally diluting the purified [$^{18}$F]-radiotracer of Formula (II) from step (iii) with a biocompatible carrier;
(v) aseptic filtration of the optionally diluted solution from step (iv) to give a radiopharmaceutical composition comprising said radiotracer.

The "biocompatible carrier" is a fluid, especially a liquid, in which the radioconjugate can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection, isotonic saline or phosphate buffer.

The "radiopharmaceutical composition" is a pharmaceutical composition comprising said radiotracer. Such compositions have their conventional meaning, and in particular are in a form suitable for mammalian administration, especially via parenteral injection. By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

The production of [$^{18}$F]-fluoride suitable for radiopharmaceutical applications is well-known in the art, and has been reviewed by Hjelstuen et al [Eur. J. Pharm. Biopharm., 78(3), 307-313 (2011)], and Jacobson et al [Curr. Top. Med. Chem., 10(11), 1048-1059 (2010)].

A non-automated radiosynthesis of Compound 1 has been reported by Okamura et al [J. Nucl. Med., 54(8), 1420-1427 (2013)].

Substituted quinolones of Formula (I) can be synthesized by conventional quinoline syntheses [Kouznetsov et al, Curr. Org. Chem., 9, 141-161 (2005)]. The syntheses of several 2-arylquinolines has been provided by Tago et al [J. Lab. Comp. Radiopharm., 57(1), 18-24 (2014)]. Further details of the precursor syntheses are provided in WO 2012/057312 A1. Thus, WO 2012/057312 A1 discloses the following synthesis of the $^{18}$F labelling precursors having alkoxy substituents at the 6-position functionalised with hydroxy and $^{18}$F groups:

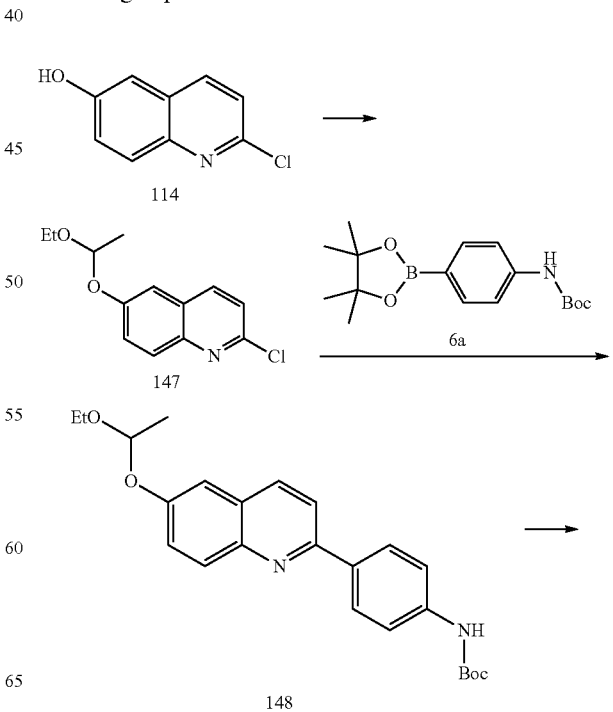

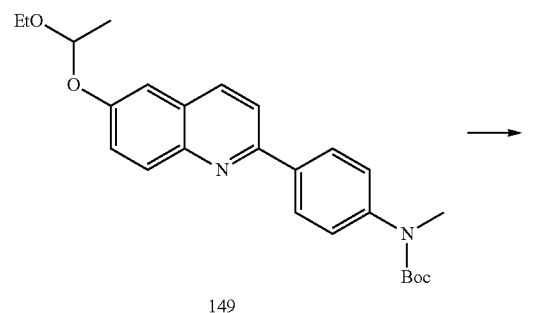

149

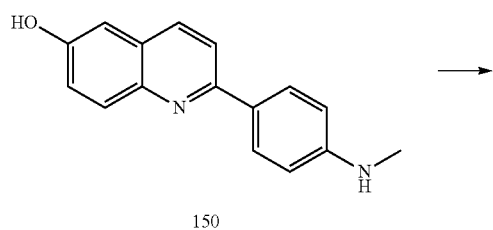

150

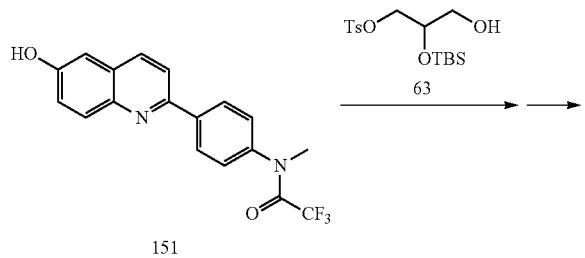

151

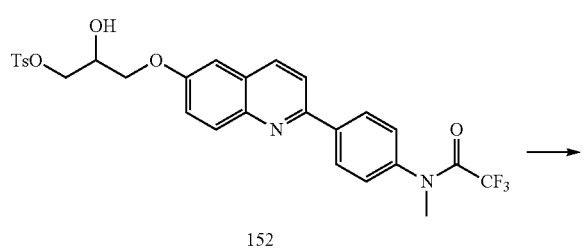

152

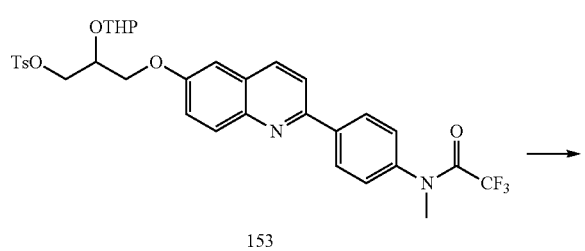

153

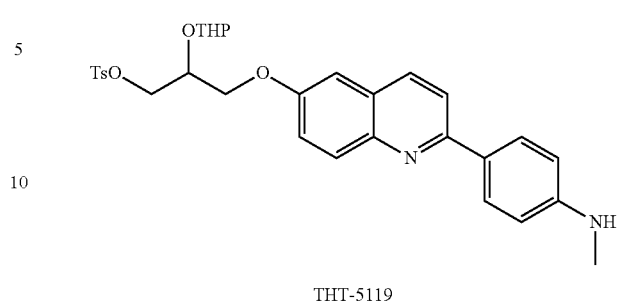

THT-5119 where: Boc = tert-butyloxycarbonyl;
TBS = tert-butyldimethylsilyl
THP = tetrahydropyran;
Ts = 4-toluenesulfonyl.

The present supporting Examples provide further experimental details. The corresponding enantiomers can be obtained by adapting the synthesis using chiral starting materials, or resolution of the racemic mixture using e.g. chiral chromatography or crystallisation of a chiral salt as is known in the art.

In a second aspect, the present invention provides a method of purification of the $^{18}$F-labelled radiotracer of Formula (II), (IIA) or (IIB) as defined in the first aspect, which comprises the SPE purification method as described in a preferred embodiment of the first aspect.

Preferred aspects of the radiotracer, precursor and purification method in the second aspect, are as described in the first aspect (above).

In a third aspect, the present invention provides a cassette as described in the first aspect (above). Preferred aspects of the cassette in the third aspect are as described in the first aspect (above).

In a fourth aspect, the present invention provides the use of the automated synthesizer apparatus as defined in the first aspect, to carry out the method of preparation of the first aspect, or the method of purification of the second aspect. Preferred aspects of the automated synthesizer apparatus and method in the fourth aspect, are as described in the first aspect (above).

In a fifth aspect, the present invention provides the use of the cassette of the third aspect, to carry out the method of preparation of the first aspect, or the method of purification of the second aspect. Preferred aspects of the cassette in the fifth aspect are as described in the third aspect (above).

BRIEF DESCRIPTION OF THE EXAMPLES

Figure 1:
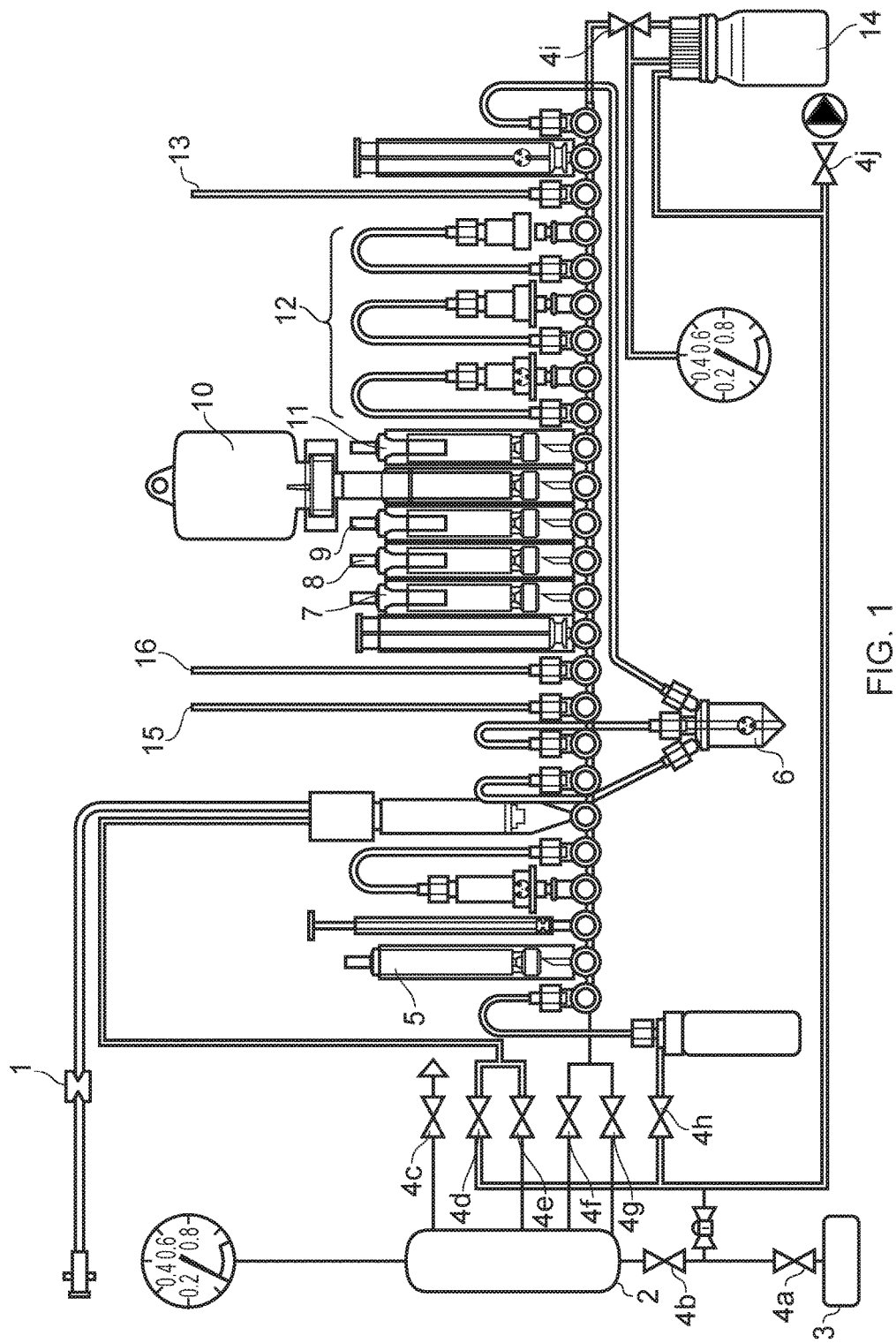
FIG. 1 and FIG. 2 illustrate exemplary cassettes of the invention useful for carrying out particular examples of the method of the invention.

The invention is illustrated by the non-limiting Examples detailed below. Example 1 provides the synthesis of a radiolabelling precursor of the invention ("Precursor 2"). Example 2 demonstrates the effect of elevated temperature on the radiosynthesis and purification of Compound 1. Example 3 provides an improved synthesis and purification of Compound 1, which is suitable for use at range of temperatures.

Compounds of the Invention

| Name | Structure |
|---|---|
| Compound 1 | [Structure: ¹⁸F-CH₂-CH(OH)-CH₂-O-quinoline-phenyl-NHMe] |
| Precursor 1 | [Structure: Ts-O-CH₂-CH(OTHP)-CH₂-O-quinoline-phenyl-NHMe] |
| Impurity A | [Structure: HO-CH₂-CH(OH)-CH₂-O-quinoline-phenyl-NHMe] |
| Impurity B | [Structure: TsO-CH₂-CH(OH)-CH₂-O-quinoline-phenyl-NHMe] |
| Precursor 2 | [Structure: TsO-CH₂-CH(OTHP)-CH₂-O-phenyl-quinoline-NHMe] |
| Compound 2 | [Structure: F-CH₂-C(H)(OH)-CH₂-O-quinoline-phenyl-NHMe, (S)-configuration] |

| Name | Structure |
|---|---|
| Precursor 3 | 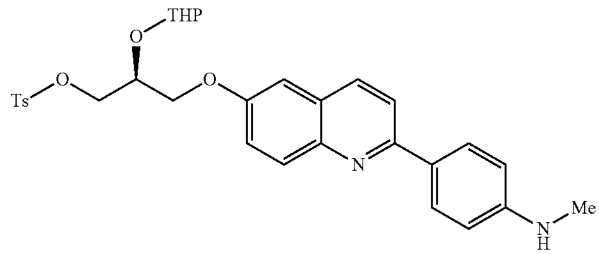 |
| Compound 3 | 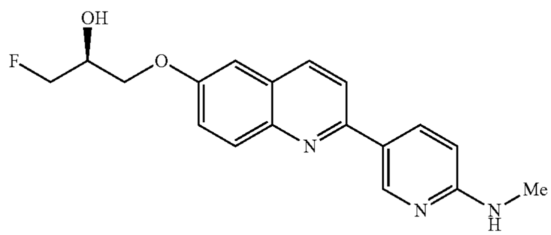 [SMILES: CNc1ccc(-c2ccc3cc(OC[C@H](O)CF)ccc3n2)cn1] |
| Precursor 4 | 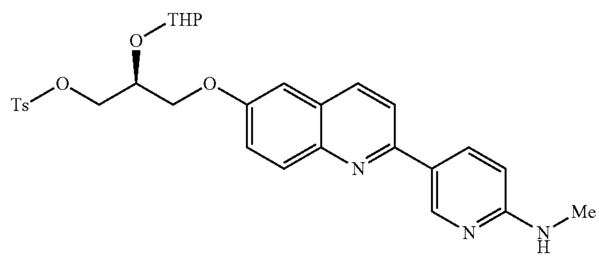 |

Abbreviations

Ac: Acetyl
Acm: Acetamidomethyl
ACN: Acetonitrile
AcOH: Acetic acid.
Boc: tert-Butyloxycarbonyl
tBu: tertiary-butyl
DCM: Dichloromethane
DIPEA: N,N-Diisopropylethyl amine
DMF: Dimethylformamide
EtOAc: ethyl acetate;
EtOH: ethanol
DMSO: Dimethylsulfoxide;
GMP: Good Manufacturing Practice;
HPLC: High performance liquid chromatography;
MeCH: acetonitrile
MW: molecular weight;
Ms: mesylate i.e. sulfonate ester of methanesulfonic acid.
RCP: radiochemical purity;
RCY: radiochemical yield;
RP-HPLC: reverse-phase high performance liquid chromatography;
SPE: solid phase extraction;
TBAF: tetrabutylammonium fluoride;
tBu: tert-butyl;
TFA: Trifluoroacetic acid;
THF: Tetrahydrofuran;
THP: tetrahydropyranyl;
TLC: thin layer chromatography;
Trt: Trityl;

Tf: triflate, i.e. sulfonate ester of trifluoromethanesulfonic acid.
Ts: tosylate, i.e. sulfonate ester of para-toluenesulfonic acid.

Example 1: Synthesis of Precursor 2

Step (a): 2-(5-Fluoro-2-nitrophenyl)-1,3-dioxolane

5-Fluoro-2-nitrobenzaldehyde (14.4 g, 85 mmol), ethane-1,2-diol (14.48 mL, 260 mmol) and 4-toluenesulfonic acid monohydrate (0.826 g, 4.34 mmol) were added to toluene (350 mL) and the mixture heated to reflux under nitrogen with a Dean & Stark condenser. The reaction was allowed to cool after 4.5 h. After 30 h, the solution was decanted from the dark sticky residue at the bottom of the flask. Added EtOAc (275 mL) and washed with saturated aqueous sodium bicarbonate (70 mL), water (140 mL), brine (70 mL) and passed through a phase separator then evaporated to dryness to give a dark brown oil (~18 g). This was dissolved in DCM:petrol (3:2) and purified by chromatography on silica gel eluting with dichloromethane (A): Petroleum ether (B) (60% B, 340 g, 15 CV, 100 mL/min) to give the expected product as a yellow oil (16.52 g, 91%).

$^1$H NMR (400 MHz,) δ 8.10-7.95 (dd, J=9.0, 4.9 Hz, 1H, Ar—H3), 7.58-7.44 (dd, J=9.1, 2.9 Hz, 1H, Ar—H4), 7.22-7.10 (ddd, J=9.1, 7.2, 2.9 Hz, 1H, Ar—H6), 6.63-6.41 (s, 1H, OC(O)H) and 4.14-3.96 (dddd, J=14.1, 8.6, 6.8, 3.3 Hz, 4H, 2×CH$_2$). $^{13}$C NMR (101 MHz,) δ 164.8 (d, J=259 Hz, C—F), 144.7 (C—NO$_2$), 137.3 (d, J=8 Hz, Ar—C1), 127.7 (d, J=9 Hz, Ar—C3), 116.5 (d, J=25 Hz, Ar—C4/6), 115.1 (d, J=25 Hz, Ar—C4/6), 99.1 (OCHO) and 65.5 (2×CH$_2$).

Step (b): 3-(1,3-Dioxolan-2-yl)-N-methyl-4-nitroaniline 2-(5-Fluoro-2-nitrophenyl)-1,3-dioxolane [Step (a), 5.21 g, 24.44 mmol] was dissolved in ethanol (37 ml) and methylamine (5.5 mL, 33 wt % in ethanol, 46.9 mmol) added. The yellow solution was stirred at ambient temperature for 10 minutes then heated to reflux for 18 h, when LCMS and TLC (1:1 DCM:petrol) showed no remaining starting material. The solution was allowed to cool and evaporated to dryness, dissolved in DCM (100 mL) and washed with saturated aqueous sodium bicarbonate (40 mL) then water (2×40 mL) and passed through a phase separator and evaporated to a deep yellow-orange oil (5.45 g, 99%).

LCMS calcd for $C_{10}H_{12}N_2O_4$: 224.1; found 225.0 [M+H]+.

$^1$H NMR (400 MHz, CDCl$_3$) δ 8.05 (d, J=9.0 Hz, 1H, Ar-5H), 6.92 (d, J=2.7 Hz, 1H, Ar-2H), 6.62 (s, 1H, CH), 6.50 (dd, J=9.1, 2.7 Hz, 1H, Ar-6H), 4.59 (br s, 1H, NH), 4.06 (m, 4H, 2×CH$_2$) and 2.94 (d, J=5.1 Hz, 3H, NCH$_3$). $^{13}$C NMR (101 MHz, CDCl$_3$) δ 153.4 (C—NH), 137.6 (C—NO$_2$), 136.4 (Ar-3C), 128.7 (Ar-5C), 110.4 (Ar-6C), 109.8 (Ar-2C), 99.9 (CH), 65.3 (2×CH$_2$) and 30.2 (N—CH$_3$).

Step (c) 5-(Methylamino)-2-nitrobenzaldehyde 3-(1,3-Dioxolan-2-yl)-N-methyl-4-nitroaniline [Step (b), 5.45 g, 24.31 mmol] was dissolved in acetone (55 mL) and hydrochloric acid (1N) (2.00 g, 55 mmol) was added and the yellow solution heated to 60 C for 3 h, when LCMS and TLC showed no residual starting material. The solution was cooled and neutralised with aqueous sodium bicarbonate and extracted into ethyl acetate (3×70 mL). The combined organics were passed through a phase separator and evaporated to give a yellow solid (4.28 g, 98%).

LCMS calcd for $C_8H_8N_2O_3$: 180.1; Found 180.92 [M+H]+.

$^1$H NMR (400 MHz, CDCl$_3$) δ 10.51 (s, 1H, HC=O), 8.10 (d, J=9.1 Hz, 1H, Ar-3H), 6.85 (d, J=2.8 Hz, 1H, Ar-6 H), 6.68 (dd, J=9.0, 2.8 Hz, 1H, Ar-4H), 4.83 (br s, 1H, N H) and 2.98 (d, J=5.1 Hz, 3H, N—CH$_3$). $^{13}$C NMR (101 MHz, CDCl$_3$) δ 190.2 (C=O), 153.8 (Ar—CNH), 137.9 (Ar—CNO$_2$), 135.6 (Ar—CCHO), 128.0 (Ar-3CH), 113.6 (Ar-4CH), 110.9 (Ar-6CH) and 30.3 (N—CH$_3$).

Step (d) 2-(4-Methoxyphenyl)-N-methylquinolin-6-amine 5-(Methylamino)-2-nitrobenzaldehyde [Step (c), 1.39 g, 7.72 mmol] was dissolved in ethanol (40 mL) in a 50 mL borosilicate tube and iron powder (1.72 g, 30.9 mmol) and hydrochloric acid (3.86 mL, 0.1N, 0.386 mmol) added and the tube sealed with PTFE/silicone screw-cap and heated in a pre-heated oil-bath at 100 C. After 2 h, the tube was removed and cooled in water and the pressure carefully released, when LCMS showed no remaining starting material. Added 1-(4-methoxyphenyl)ethanone (1.16 g, 7.72 mmol) and powdered potassium hydroxide (0.52 g, 9.26 mmol) to the mixture, resealed and heated at 100 C for 22 h. Cooled, diluted with water (150 mL) and extracted with DCM (4×50 mL), washed combined organics with water (50 mL) and passed through a phase separator and evaporated to give a yellow-brown gum (1.94 g). This was purified by chromatography on silica gel eluting with petroleum ether (A): ethyl acetate (B) (10-100% B, 100 g, 15 CV, 85 mL/min) to give a pale yellow solid (530 mg, 26% yield).

LCMS calcd for $C_{17}H_{16}N_2O$ 264.1; found 265.0 [M+H]+.

$^1$H NMR (400 MHz, CDCl$_3$) δ 8.12-8.01 (m, 2H, Ph-H), 7.94 (d, J=8.6 Hz, 1H, Ar—H), 7.90 (d, J=9.1 Hz, 1H, Ar—H) 7.68 (d, J=8.6 Hz, 1H, Ar—H), 7.05 (dd, J=9.0, 2.6 Hz, 1H, Ar—H), 7.01 (m, 2H, Ph-H), 6.66 (d, J=2.5 Hz, 1H, Ar—H), 4.03 (br s, 1H, NH), 3.58 (s, 3H, OCH$_3$), 2.90 (s, 3H, NCH$_3$). $^{13}$C NMR (101 MHz, CDCl$_3$) δ 160.2 (C—OMe), 152.9 (Ar—C—N), 147.0 (C—NMe), 143.2 (Ar—C10), 134.6 (Ar—C-4), 132.9 (Ph-C1), 130.4 (Ar—C7), 128.8 (Ar—C9), 128.4 (Ph-C2&6), 121.4 (Ar—C8), 118.9 (Ar—C3), 114.2 (Ph-C3&5), 102.5 (Ar—C5), 55.5 (O—CH$_3$) and 30.8 (N—CH$_3$).

Step (e) 4-(6-(Methylamino)quinolin-2-yl)phenol 2-(4-Methoxyphenyl)-N-methylquinolin-6-amine [Step (d), 680 mg, 2.57 mmol] was dissolved in DCM (35 mL) and boron tribromide (10.3 mL, 1M in DCM, 10.3 mmol) was added and the mixture stirred for 18 h—some insoluble gum formed—when LCMS showed mainly desired product with a little residual starting material. Added methanol (2-3 mL dropwise) to destroy excess BBr$_3$ and filtered off the yellow solid. Stirred with saturated aqueous sodium bicarbonate and filtered. Allowed to dry on filter paper to give the desired product as a yellow solid (602 mg, 93%).

LCMS calcd for $C_{16}H_{14}N_2O$ 250.1; found 251.0 [M+H]+.

$^1$H NMR (400 MHz, d$_6$-DMSO) δ 7.96 (m, 3H), 7.77 (d, J=8.7 Hz, 1H, C8-H), 7.65 (d, J=9.0 Hz, 1H, C4-H), 7.11 (dd, J=9.1, 2.0 Hz, 1H, C3-H), 6.81 (d, J=8.5 Hz, 2H, C2' &6'-H), 6.59 (m, 1H, C5-H), 6.13 (d, J=4.8 Hz, 1H, NH) and, 2.74 (d, J=4.8 Hz, 3H, N—CH$_3$). $^{13}$C NMR (101 MHz, d$_6$-DMSO) δ 159.3 (C—OH), 151.6 (C6-N), 148.0 (C9), 142.4 (C4'), 134.6 (C4-H), 129.9 (C7-H), 129.0 (C10), 128.3 (C3-H'& C5'-H), 122.1 (C8-H), 118.4 (C3-H), 116.1 (C2'-H & C6'-H), 101.2 (C5-H) and 30.3 (N—CH$_3$).

Step (f) 3-(4-(6-(Methylamino)quinolin-2-yl)phenoxy)-2-((tetrahydro-2H-pyran-2-yl)oxy)propyl 4-methylbenzenesulfonate 4-(6-(Methylamino)quinolin-2-yl)phenol [Step (e), 300 mg, 1.2 mmol] and potassium carbonate (215 mg, 1.56 mmol) were mixed in a 25 mL rb flask fitted with a rubber septum and a nitrogen balloon. Dry DMF (10 mL) was added followed by 2-((tetrahydro-2H-pyran-2-yl)oxy)propane-1,3-diyl bis(4-methylbenzenesulfonate) (581 mg, 1.2 mmol) [Oh et al, Nucl. Med. Biol., 32(8), 899-905 (2005)], and the mixture stirred vigorously and heated at an external temp of 90 C. Cooled after 22 h, when TLC showed incomplete reaction. Nevertheless, ice water (30 mL) was added and the organic material extracted into ethyl acetate (3×15 mL). Washed the combined organics with water (2×15 mL), brine (15 mL) and passed through a phase separator and evaporated. TLC (EtOAc:petrol 1:1) and LCMS showed the 2 main peaks as starting material and product. Adsorbed onto silica from ethyl acetate and acetonitrile mixture and purified by chromatography on silica gel eluting with petroleum ether (A): ethyl acetate (B) (10-100% B, 50 g, 20 CV, 40 mL/min) to give the major peak being product but contaminated by starting material. Re-purified by chromatography on silica gel eluting with dichloromethane (A): ethyl acetate (B) (20-60% B with initial isocratic at 21%, 25 g, 25 CV, 40 mL/min) to give pure product as a yellow solid (65 mg, 10%).

LCMS calcd for $C_{31}H_{34}N_2O_6S$ 562.2; found 563.0 [M+H]+.

$^1$H NMR (400 MHz, CDCl$_3$) δ 8.02 (m, 2H, C3'-H & C5'-H), 7.96 (d, J=8.6 Hz, 1H, C7-H), 7.90 (d, J=9.1 Hz, 1H), 7.77 (m, 2H), 7.69 (d, J=8.6 Hz, 1H), 7.26 (m, 2H), 7.08 (dd, J=9.0, 2.6 Hz, 1H), 6.89 (m, 2H), 6.68 (d, J=2.5 Hz, 1H), 4.81 (t, J=3.3 Hz, 1H), 4.40-3.94 (m, 3H), 2.99-2.89 (s, 1H), 2.37 (s, 3H, Ar—CH$_3$), 1.86-1.63 (m, 2H), 1.61-1.44 (m, 3H). $^{13}$C NMR (101 MHz, CDCl$_3$) δ 158.9, 158.8, 152.6, 147.1, 145.0, 143.1, 134.6, 133.3, 132.6, 130.4, 130.0, 129.9, 128.9, 128.3, 128.1, 128.0, 121.5, 118.8, 114.8, 102.4, 99.1, 98.5, 72.7, 72.3, 69.4, 69.1, 66.9, 66.2, 62.9, 62.3, 60.5, 30.8, 30.6, 30.5, 25.4, 21.8, 21.2, 19.5, 19.1 and 14.3.

Example 2: Effect of Temperature on the Automated Radiosynthesis of Compound 1

[$^{18}$F]-fluoride was produced using a GE PETtrace cyclotron with a silver target via the [$^{18}$O](p,n) [$^{18}$F] nuclear reaction. Total target volumes of 3.2-4.8 mL were used. The radiofluoride was trapped on a Waters QMA cartridge (pre-conditioned with potassium carbonate), and the [$^{18}$F]-fluoride was eluted with a solution of TBAF bicarbonate (0.75 M, 160 µL) in acetonitrile (640 µL). Nitrogen was used to drive the solution off the QMA cartridge to the reaction vessel. The [$^{18}$F]-fluoride was dried for 9 minutes at 120° C. under a steady stream of nitrogen and vacuum.

To investigate the impact of the anticipated PET cell temperature range on the efficacy of the SPE process, radiosynthesis studies were conducted at the upper end of the range (35° C.) with a single Waters tC18+ SPE cartridge.

A cassette was fitted to a FASTlab synthesiser apparatus (GE Healthcare). [$^{18}$F]Fluoride was transferred via the activity inlet of the FASTlab cassette using vacuum. The activity was transferred from the activity inlet to the (pre-treated) QMA cartridge where the [$^{18}$F] was trapped and the water passed through to the $^{18}$O water recovery vial, using a combination of N2 to push and vacuum to pull. After the transfer of the eluent containing the $^{18}$F-activity into the reaction vessel, the solvents were evaporated to dryness. The evaporation was carried out with heating under nitrogen flow and under vacuum.

Precursor 1 (1.8 mL of a 1.5 mg/mL solution in DMSO) was added to the dry residue. Nucleophilic substitution at 130° C. was carried out in the closed reaction vessel, in which the tosylate group of the precursor was replaced by the $^{18}$F-ions. After labelling, the solution was cooled to 70° C. The tetrahydropyranylated intermediate was converted into Compound 1 by removing the THP protecting group. This deprotection was carried out in the reaction vessel by the addition of aqueous HCl (0.35 mL of 4M HCL diluted with 0.82 mL of water), heating at 90° C. for 35 seconds, followed by quenching via the addition of 4% aqueous ammonia solution (1.4 mL).

The resulting Compound 1 was obtained in a DMSO/aqueous mixture, and was adjusted to an 80:20 aqueous:organic mixture, prior to loading onto two Waters tC18+ SPE cartridges in series.

Analysis of fractions of the 40% acetonitrile wash volume collected from the FASTlab™ combined with reduced RCY showed significant loss of radiotracer. GE FASTlab™ log files were used to determine that very low wash volumes were sufficient to completely elute all the radiotracer at 35° C.

Example 3: Automated Radiosynthesis of Compound 1

The radiosynthesis of Example 2 was adapted using a third Waters tC18+ cartridge added to the GE FASTlab™ cassette and this layout was studied over the temperature range from 19.3° C.- to 37.0° C. FIG. 1 illustrates the cassette layout used wherein 1 indicates the activity inlet, 2 a buffer volume, 3 a supply of N$_2$, each of 4a-j a valve, 5 effluent, 6 is the reaction vessel, 7-10 are reagent positions wherein 7 is precursor, 8 is 4M HCl, 9 is 4% ammonia, 10 is water and 11 is vacant. Reference number 12 indicates the three Waters tC18+ cartridges, 13 the product outlet, 14 the waste bottle, 15 40% MeCN and 16 100% EtOH.

The resulting Compound 1 was obtained in an acetonitrile/aqueous mixture, and was adjusted to an 80:20 aqueous:organic mixture, prior to loading onto three Waters tC18+ SPE cartridges in series. The SPE cartridges were then rinsed with water and washed with 10.6 mL of 40% aqueous acetonitrile to remove Impurity A prior to elution of Compound 1 with ethanol.

The Compound 1 obtained had a total chemical content of 5-10 µg/mL and radiochemical purity (RCP) in the range 92 to 97% at a specific activity of 100-1000 GBq/µmol, for starting $^{18}$F activities in the range 40-60 GBq. In addition, by studying SPE wash fractions (via collecting the samples and analysing information provided by the radio detectors in the GE FASTlab™ log file), it was noted that product losses were negligible and hence good radiochemical yield (RCY) was achieved. Chemical content, RCY and specific activity measurements were not observed to be affected by the addition of a third SPE cartridge.

Example 4: Automated Radiosynthesis of Compounds 2 & 3

Figure 2:
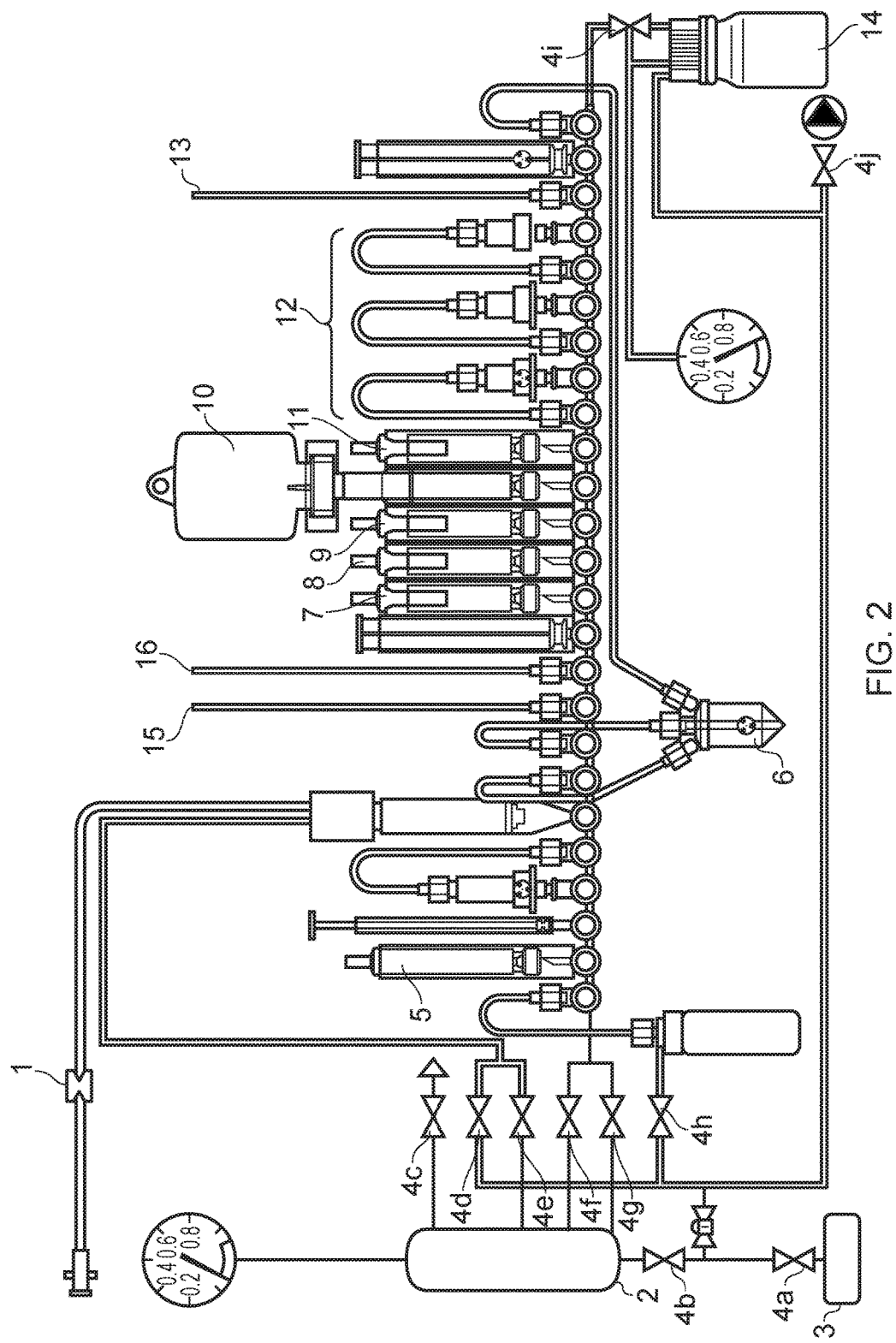

The cassette layout of FIG. 2 was used to synthesise Compounds 2 & 3. In FIG. 2: 1 indicates the activity inlet, 2 a buffer volume, 3 a supply of N$_2$, each of 4a-j a valve, 5 effluent, 6 is the reaction vessel, 7-10 are reagent positions wherein 7 is precursor (Precursor 3 and Precursor 4, respectively for Compound 2 and Compound 3), 8 is DMSO, 9 is 4M HCl, 10 is water and 11 is 4% ammonia. Reference number 12 indicates the three Waters tC18+ cartridges, 13 the product outlet, 14 the waste bottle, 15 is MeCN (40% and 28.5% for Compound 2 and Compound 3, respectively) and 16 100% EtOH. Precursors 2 and 4 were obtained using methods similar to that for Precursor 1 (i.e. as per methods described in Okamura et al J. Nucl. Med., 54(8), 1420-1427 (2013)).

For Compound 2, 11 mL of 40% MeCN was required to give a chemical content of 0.1-1.9 µg/mL over the temperature range from 21° C.-39° C. A decay corrected yield of 42-57% was obtained when using 4 mg of precursor. The RCP was >90% when starting with 60 GBq or less.

For Compound 3, 11.5 mL of ca. 28.5% MeCN was required to give a chemical content of <1.0 µg/mL over the temperature range 20-30° C. Decay corrected yields of 20-25% were obtained with 3 mg precursor. For this compound, the starting activity was increased to 100 GBq without any affect of RCP, showing RCP's of >98%. However, the SPE purification works at a tighter temperature range as compared to THK5317. At around 25° C. and below, the product is trapped on the 2$^{nd}$ SPE cartridge and is eluted into the product vial, whereas at around 26-30° C. the product is trapped on the 3$^{rd}$ SPE cartridge before being eluted into the product vial. Above 30° C. some of the product is washed to waste and the resulting yield is thus decreased. Therefore, the operating temperature for THK5351 is 20-30° C.

The invention claimed is:

1. An automated method of preparation of an $^{18}$F-labelled radiotracer of Formula (II) in an automated synthesizer, which comprises a microprocessor and an interchangeable, disposable cassette which comprises a reaction vessel, a supply of solvents suitable for the preparation and purification of said radiotracer, and a supply of the precursor of Formula (I):

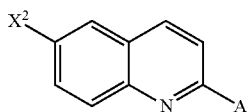
(I)

the method comprising,
(i) transferring said precursor of Formula (I) to said reaction vessel, followed by reacting said precursor with [$^{18}$F]-fluoride in a suitable solvent, and removing the Pg$^1$ protecting group, to give the $^{18}$F-labelled radiotracer of Formula (II) in a reaction mixture,

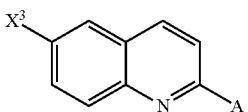
(II)

wherein the cassette further comprises at least two C 18-reverse phase solid phase extraction (SPE) columns connected in series, and said method further comprising:
(ii) loading the reaction mixture containing the $^{18}$F-labelled radiotracer of Formula (II) from step (i) onto the at least two SPE columns connected in series to trap the $^{18}$F-labelled radiotracer of Formula (II) onto the SPE columns, and eluting the $^{18}$F-labelled radiotracer of Formula (II) with the solvent(s) of said cassette to obtain the $^{18}$F-labelled radiotracer of Formula (II):
wherein the microprocessor-controlled SPE purification does not comprise HPLC; wherein:
A is chosen from:

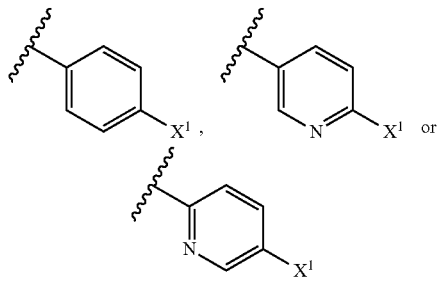

$X^1$ and $X^2$ are independently an $X^a$ or an $X^b$ group;
$X^3$ is an $X^a$ or an $X^c$ group;
$X^a$ is $NR^1R^2$;
$X^b$ is

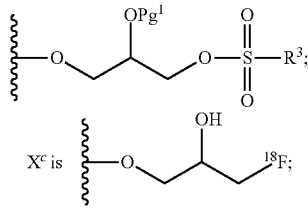

$X^c$ is

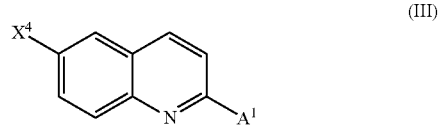

$R^1$ and $R^2$ independently comprise H or $C_{1-4}$ alkyl, or $R^1$ and $R^2$ together with the N atom and optionally the phenyl ring to which they are attached comprise a 5- or 6-membered nitrogen-containing aliphatic or heteroaromatic ring, optionally incorporating one further heteroatom chosen from —O—, —S—, =N— and —NR$^a$—, where R$^a$ is H or $C_{1-4}$ alkyl;
$R^3$ is $C_{1-4}$ alkyl, $C_{1-4}$ haloalkyl, $C_{5-8}$ aryl or $C_{6-12}$ aralkyl;
Pg$^1$ is an alcohol protecting group;
provided that in Formula (I), one $X^b$ group is present, and in Formula (II) one $X^c$ group is present.

2. The method of claim 1,
where step (i) is carried out by:
(a) reacting the precursor of Formula (I) with [$^{18}$F]-fluoride in a suitable solvent, to give an $^{18}$F-labelled intermediate of Formula (III):

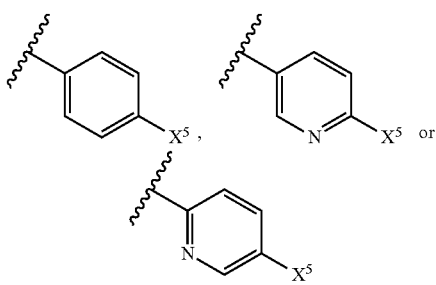
(III)

wherein
$A^1$ is chosen from:

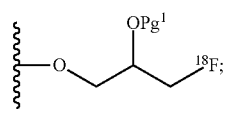

$X^4$ and $X^5$ are each independently an Xa or $X^d$ group; where $X^d$ is:

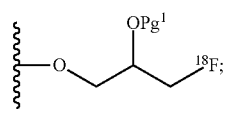

provided that, in Formula (III) one $X^d$ group is present; then:

(b) removing the Pg¹ protecting group from said intermediate to give the ¹⁸F-labelled radiotracer of Formula (II).

3. The method of claim 2, where $X^2$ is $X^b$, such that the precursor is of Formula (IA):

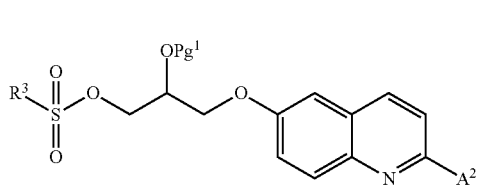
(IA)

and the radiotracer product is of Formula IIA:

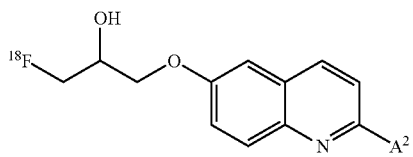
(IIA)

where $A^2$ is chosen from:

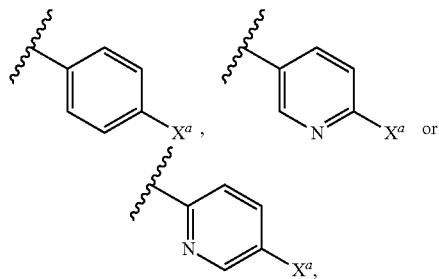

where $X^a$ is as defined.

4. The method of claim 3, where the precursor is the S-enantiomer of Formula (IB):

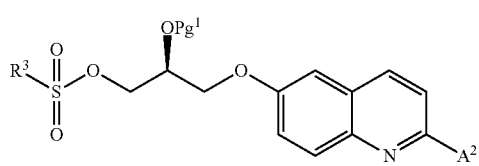
(IB)

and the radiotracer product is the S-enantiomer of Formula (IIB):

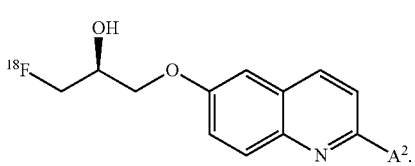
(IIB)

5. The method of claim 4, where A is an $A^2$ group of formula:

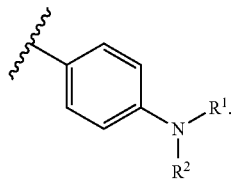

6. The method of claim 5, where —NR¹R² is —NHCH₃ or —N(CH₃)₂.

7. The method of claim 1, where the C18-reverse phase SPE columns comprise C 18-silica.

8. The method of claim 1, wherein step (ii) is carried out at 15 to 40° C. with three SPE columns connected in series.

9. The method of claim 1, wherein after trapping the radiotracer of Formula (II), the SPE columns connected in series are first eluted with an aqueous, water-miscible organic solvent to remove impurities, and then eluted with ethanol to elute the radiotracer of Formula (II).

10. The method of claim 1, further comprising:
   (iii) optionally diluting the purified [¹⁸F]-radiotracer of Formula (II) from step (ii) with a biocompatible carrier; and
   (iv) aseptically filtering the optionally diluted solution from step (iii) to give a radiopharmaceutical composition comprising said radiotracer of Formula (II).

11. The method of claim 1 further comprising adding water to the reaction mixture of step (i) to increase the water and organic solvent ratio of the reaction mixture before conducting step (ii).

12. An automated method of preparing an ¹⁸F-labelled radiotracer of Formula (IIA) in an automated synthesizer, which comprises a microprocessor and an interchangeable, disposable cassette which comprises a reaction vessel, a supply of solvents suitable for the preparation and purification of said radiotracer, three C 18-reverse phase solid phase extraction (SPE) columns connected in series, and a supply of the precursor of Formula (IA):

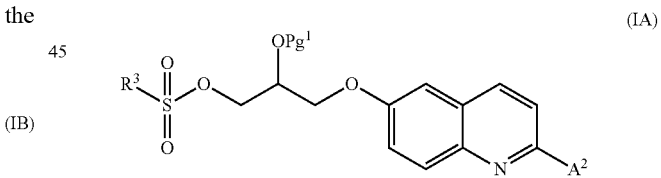
(IA)

the method comprising,
(i) transferring said precursor of Formula (IA) to said reaction vessel, followed by reacting said precursor with [¹⁸F]-fluoride in a suitable solvent, and removing the Pg¹ protecting group, to give the ¹⁸F-labelled radiotracer of Formula (IIA) in a reaction mixture,

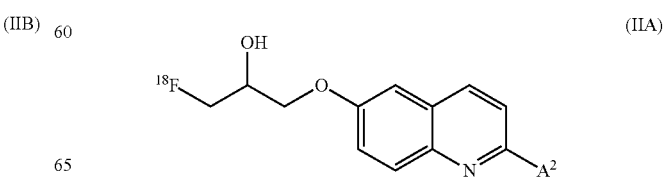
(IIA)

where $A^2$ is chosen from:

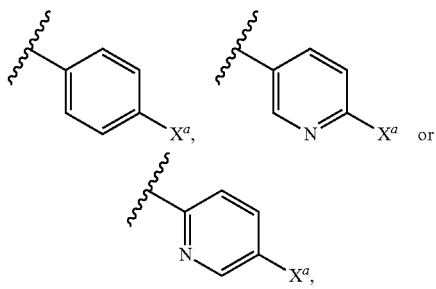

where $X^a$ is $NR^1R^2$;
$R^3$ is $C_{1-4}$ alkyl, $C_{1-4}$ haloalkyl, $C_{5-8}$ aryl or $C_{6-12}$ aralkyl;
$Pg^1$ is an alcohol protecting group,
(ii) adding water to the reaction mixture of step (i) to increase the water and organic solvent ratio to form a diluted reaction mixture containing the $^{18}F$-labelled radiotracer of Formula (IIA),
(iii) loading the diluted reaction mixture containing the $^{18}F$-labelled radiotracer of Formula (IIA) from step (ii) onto the three SPE columns connected in series to trap the $^{18}F$-labelled radiotracer of Formula (IIA) onto the SPE columns, and eluting the $^{18}F$-labelled radiotracer of Formula (IIA) with the solvent(s) of said cassette to obtain the $^{18}F$-labelled radiotracer of Formula (IIA);
wherein the microprocessor-controlled SPE purification does not comprise HPLC.

13. The method of claim 12, wherein —$NR^1R^2$ is —$NHCH_3$ or —$N(CH_3)_2$.

14. The method of claim 12, wherein after trapping the radiotracer of Formula (IIA), the three SPE columns connected in series are first washed with water, eluted with aqueous acetonitrile to remove impurities, and then eluted with ethanol to elute the radiotracer of Formula (IIA).

15. The method of claim 12, further comprising:
(iv) optionally diluting the purified [$^{18}F$]-radiotracer of Formula (II) from step (iii) with a biocompatible carrier; and
(v) aseptically filtering the optionally diluted solution from step (iv) to give a radiopharmaceutical composition comprising said radiotracer of Formula (IIA).

16. The method of claim 12, wherein step (iii) is carried out at 20 to 30° C.

* * * * *